United States Patent [19]

Zengel et al.

[11] Patent Number: 4,670,556

[45] Date of Patent: Jun. 2, 1987

[54] PROCESS FOR THE PRODUCTION OF THIAZOLYL-2-SULPHENAMIDES

[75] Inventors: Hans Zengel, Kleinwallstadt; Ludwig Eisenhuth, Obernburg-Eisenbach; Manfred Bergfeld, Erlenbach, all of Fed. Rep. of Germany

[73] Assignee: AKZO NV, Arnhem, Netherlands

[21] Appl. No.: 628,261

[22] Filed: Jul. 6, 1984

[30] Foreign Application Priority Data

Jul. 16, 1983 [DE] Fed. Rep. of Germany ....... 3325724

[51] Int. Cl.[4] .......................................... C07D 277/80
[52] U.S. Cl. ................................... 544/135; 544/368; 546/198; 548/167; 548/168; 540/544; 540/553; 540/575; 540/602
[58] Field of Search ................ 548/167, 168; 546/198; 544/135, 368; 540/544, 553, 575, 602

[56] References Cited

U.S. PATENT DOCUMENTS

| 3,549,650 | 12/1970 | D'Amico | 548/168 |
| 4,182,873 | 1/1980 | Janin | 548/168 |
| 4,258,197 | 3/1981 | Toukan | 548/168 |

FOREIGN PATENT DOCUMENTS

| 4896 | 3/1979 | European Pat. Off. | 548/168 |
| 29718 | 3/1981 | European Pat. Off. | 548/168 |
| 2356686 | of 1974 | Fed. Rep. of Germany | 548/168 |
| 1695533 | 2/1974 | Fed. Rep. of Germany | 548/168 |
| 2349934 | 4/1974 | Fed. Rep. of Germany | 548/168 |
| 2726901 | 1/1979 | Fed. Rep. of Germany | 544/135 |
| 3127193 | 5/1982 | Fed. Rep. of Germany | 548/168 |
| 1407649 | 9/1975 | United Kingdom | 548/168 |
| 2080294 | 2/1982 | United Kingdom | 548/168 |

*Primary Examiner*—Robert T. Bond
*Attorney, Agent, or Firm*—Parkhurst & Oliff

[57] ABSTRACT

This invention relates to a process for the production of benzothiazolyl sulphenamides corresponding to the following general formula:

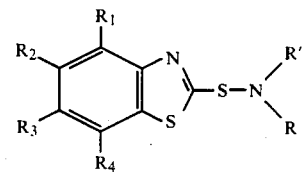

in which a corresponding 2-mercaptobenzothiazole or a dibenzothiazolyl-2,2'-disulphide is reacted with a primary or secondary amine at temperatures of from 0 to 100° C. in the presence of ammonia, oxygen, a copper-containing catalyst and a reaction medium containing an excess of the primary or secondary amine or of a mixture of that amine with water and/or a water-miscible organic solvent.

Benzothiazolyl sulphenamides are valuable vulcanization accelerators.

8 Claims, No Drawings

PROCESS FOR THE PRODUCTION OF THIAZOLYL-2-SULPHENAMIDES

BACKGROUND OF THE INVENTION

This invention relates to a process for the production of benzothiazolyl-2-sulphenamides from 2-mercaptobenzothiazoles or dibenzothiazolyl-2,2'-disulphides and primary or secondary amines in the presence of oxygen and a copper-containing catalyst in a solvent.

Sulphenamides are used in large quantities as vulcanization accelerators.

There are several known processes for the production of sulphenamides. On an industrial scale, they are produced by the oxidative condensation of 2-mercaptothiazoles with an amine using such oxdizing agents as, for example, chlorine, iodine or hypochlorite, hydrogen peroxides or other peroxides (E. L. Carr, J. Org. Chem. 14 921 (1948), U.S. Pat. Nos. 2,191,657, 2,417,989, 2,419,283, 3,144,652, French Pat. No. 841,753, British Pat. No 655,668 and German Offenlegungsschrift No. 31 27 193). In addition, it is known that sulphenamides may be obtained by replacing the amide in an N-substituted thiazolyl-2-sulphenamide by another amide (Offenlegungsschrift No. 19 41 884), by the ammonolysis of dithiazolyl disulphide (British Pat. No. 377,370, U.S. Pat. Nos. 2,100,692, 2,214,460 and 2,226,767) and also by electrochemical oxidation (Offenlegungsschrift No. 27 44 423; and J. Org. Chem. 43 (16) 3223 (1978)).

It is also known that oxygen may be used as an oxidizing agent in the oxidative reaction of 2-mercaptothiazoles or dithiazolyl-2,2'-disulphides with an amine. In the processes according to Canadian Pat. No. 863,531, U.S. Pat. No. 3,737,431 and European Patent Application No. 29 718, metal phthalocyanines are used as the catalyst. However, problems are involved in the industrial production and handling of such catalysts as these which are both sensitive and expensive. In addition, the processes according to these three publications only give moderate to poor yields or involve elaborate process steps for isolating the end product.

In addition, it is known from German Offenlegungsschrifts Nos. 23 49 934 and 23 56 686 (to which U.S. Pat. No. 4,182,873 substantially corresponds), that the reaction of 2-mercaptothiazoles or dithiazolyl-2,2'-disulphides with amines may be carried out in the presence of oxygen and copper or another of its derivatives such as the copper phthalocyanine complexes. Temperatures of from 0° to 200° C. and oxygen partial pressures of from 0.1 to 30 bars are preferably applied in that process. In addition, the reaction is said to be preferably carried out in water or an organic solvent, the solvent used being said to be in particular the excess of the amine used for the reaction with the 2-mercaptobenzothiazole. As the Comparison Examples of these two German Offenlegungsschrifts show, however, these known processes only give relatively low yields of sulphenamide. As further studies have shown, this is quite clearly attributable to the fact that, under the conditions applied, the sulphenamide formed is further oxidized to a considerable extent to secondary products (for example benzothiazolyl sulphonic acids, benzothiazole, sulphates, etc.). In this process, therefore, part of the valuable end product is lost. Accordingly, the selectivities obtainable in this process are totally inadequate for economic application.

SUMMARY OF THE INVENTION

Accordingly, there was a need to overcome the disadvantages of known processes. An object of the present invention, therefore, is to provide a process by which the 2-mercaptobenzothiazoles or dibenzothiazolyl-2,2'-disulphides may be reacted with amines and oxygen at a high reaction velocity and with high selectivity to form high yields of sulphenamides.

DETAILED DESCRIPTION OF THE INVENTION

According to the present invention, this object is achieved by a process for the production of benzothiazolyl sulphenamides corresponding to the following general formula:

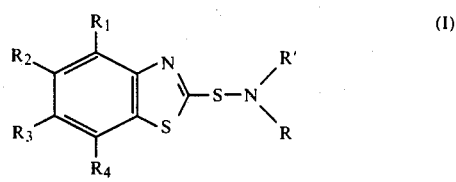

wherein:

$R_1$, $R_2$, $R_3$ and $R_4$, which may be the same or different from each other, each represents hydrogen, chlorine, a nitro group, a hydroxyl group, a $C_1$–$C_6$ alkyl or alkoxyl radical, a $C_6$–$C_{12}$ cycloalkyl or aryl radical; and R and R', which may be the same or different from each other, each represents a $C_{1-18}$ straight, branched or cyclic alkyl group, and may be attached to one another through a heteroatom and/or carbon atoms so that, with the nitrogen, they form a heterocyclic group containing one or more heteroatoms; or R represents a hydrogen atom and R' represents a straight, branched or cyclic $C_3$–$C_8$ alkyl group;

by reacting a 2-mercaptobenzothiazole or dibenzothiazolyl-2,2'-disulphide corresponding to the following general formulae:

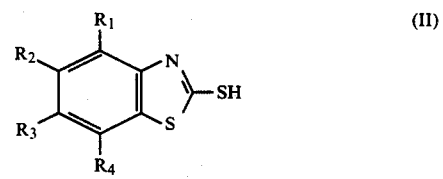

or

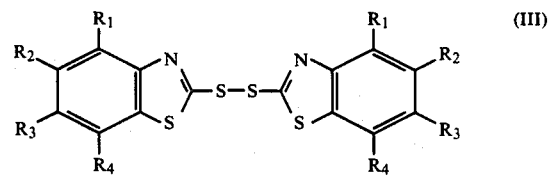

wherein $R_1$, $R_2$, $R_3$ and $R_4$ are as defined above; with a primary or secondary amine corresponding to the following general formula:

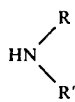

(IV)

wherein R and R' are also as defined above; in the presence of oxygen or an oxygen-containing gas and copper or a copper derivative at temperatures of from 0° to 100° C., characterized in that the reaction is carried out in the presence of ammonia and an excess of the above-mentioned primary or secondary amine or a mixture of that excess amine with water and/or with a water miscible organic solvent as the reaction medium.

The substituents $R_1$, $R_2$, $R_3$ and $R_4$ in general formulae (I) to (III) are preferably a chlorine atom, a hydroxyl group, a nitro group, a straight- or branched-chain $C_1$–$C_4$ alkyl radical, such as methyl, ethyl, propyl, isopropyl, butyl or t-butyl, a $C_1$–$C_4$ alkoxy radical, such as methoxy, ethoxy, propoxy or butoxy, or a phenyl, tolyl, ethyl phenyl, nitrophenyl, chlorophenyl or naphthyl radical.

The process according to the present invention is particularly suitable for the production of sulphenamides of 2-mercaptobenzothiazole, the most important representative of the 2-mercaptothiazoles. The following compounds are examples of other 2-mercaptothiazoles which are suitable for use as starting materials for the production of the thiazolyl-2-sulphenamides corresponding to general formula (I): 2-mercapto-4-methylbenzothiazole, 2-mercapto-5-methylbenzothiazole, 2-mercapto-6methylbenzothiazole, 2-mercapto-4,5-dimethylbenzothiazole, 2-mercapto-4-phenylbenzothiazole, 2-mercapto-4-methoxybenzothiazole, 2-mercapto-6-methoxybenzothiazole, 2-mercapto-5,6-dimethoxybenzothiazole, 2-mercapto-6-methoxy-4-nitrobenzothiazole, 2-mercapto-6-ethoxybenzothiazole, 2-mercapto-4-chlorobenzothiazole, 2-mercapto-5-chlorobenzothiazole, 2-mercapto-6-chlorobenzothiazole, 2-mercapto-7-chlorobenzothiazole, 2-mercapto-5-chloro-6-methoxybenzothiazole, 2-mercapto-5-chloro-4-nitrobenzothiazole, 2-mercapto-5-chloro-6-nitrobenzothiazole, 2-mercapto-4,5-dichlorobenzothiazole, 2-mercapto-4,7-dichlorobenzothiazole, 2-mercapto-5-nitrobenzothiazole, 2-mercapto-6-nitrobenzothiazole, 2-mercapto-4-phenylbenzothiazole, 2-mercaptonaphthothiazole and 2-mercapto-6-hydroxybenzothiazole.

Instead of the mercaptothiazoles mentioned above, the corresponding dithiazolyl-2,2'-disulphides may be used equally effectively as starting materials for the process according to the present invention. The following compounds are specific examples of such dithiazolyl-2,2'-disulphides: dibenzothiazolyl-(2,2')-disulphide, bis-[6-methylbenzothiazolyl-(2)]-disulphide, bis-[4-methylbenzothiazolyl-(2)]-disulphide, bis-[4-methoxybenzothiazolyl-(2)]-disulphide, bis-[6-ethoxybenzothiazolyl-(2)]-disulphide, bis-[5-chlorobenzothiazolyl-(2)]-disulphide, bis-[5-chloro-4-nitrobenzothiazolyl-(2)]-disulphide, bis-[3-chloro-6-nitrobenzothiazolyl-(2)]-disulphide, bis-[6-nitrobenzothiazolyl-(2)]-disulphide. Dibenzothiazolyl-(2,2')-disulphide is preferably used.

Primary amines suitable for use in the process according to the present invention are, for example, n-propylamine, isopropylamine, n-butylamine, sec.-butylamine, t-butylamine, pentylamine, hexylamine, heptylamine, octylamine, decylamine, cyclopentylamine, cyclohexylamine, cycloheptylamine, cyclooctylamine or benzylamine. Suitable secondary amines are, for example, diethylamine, di-n-propylamine, diisopropylamine, di-n-butylamine, di-t-butylamine, dicyclohexylamine, pyrrolidine, piperidine, piperazine, morpholine, 2,6-dimethylmorpholine and 3,5-dimethylmorpholine. Preferred amines are cyclohexylamine, t-butylamine and morpholine. However, the amines suitable for use in accordance with the present invention are by no means confined to those listed here.

The addition of ammonia in accordance with the present invention has the surprising effect that, even in the presence of an excess of the oxygen used as oxidizing agent, the reaction stops at the desired sulphenamide. Accordingly, the reaction is easy to regulate; above all, there are no losses of yield or impurities in the end product as a result of over-oxidation (also reflected in the large excess of oxidizing agent required in the prior art), as would be the case if the reaction was carried out in the absence of ammonia, for example in accordance with Offenlegungsschrifts Nos. 23 49 934 and 23 56 686. In addition, the ammonia provides for a considerable increase in the reaction velocity. In many cases, no reaction whatever with the oxygen takes place in the absence of ammonia.

However, the addition of ammonia in accordance with the present invention, even in a large excess, does not in any circumstances result in the formation of a sulphenamide corresponding to the following general formula:

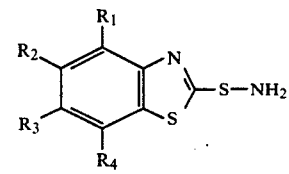

Instead, it is only the desired N-substituted sulphenamide which is formed with a high degree of selectivity. According to the teaching of German Offenlegungsschrifts Nos. 23 49 934 and 23 56 686, a sulphenamide which is unsubstituted on the nitrogen is said to be formed with ammonia (instead of a secondary or primary amine). In actual fact, however, it is the corresponding dibenzothiazolyl disulphide which is formed in that case (cf. German Offenlegungsschrift No. 31 13 298):

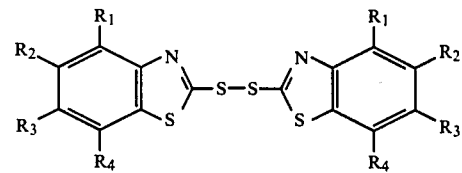

The quantity of ammonia used in accordance with the present invention may be varied within wide limits. Even an addition of only 0.2% by weight of ammonia, based on the weight of the reaction mixtures, produces a favorable effect. It is advisable not to exceed an addition of 25% by weight of ammonia. It is particularly advantageous to add from 1 to 15% by weight of ammonia, based on the weight of the reaction mixture.

The choice of the reaction medium is important to the process according to the present invention for obtaining relatively high yields and selectivity levels and is determined in particular by the type of primary or secondary amine to be reacted.

In some cases, it is preferred to use an excess of the particular amine as the sole reaction medium. In many other cases, it is advantageous to use a mixture consisting of the particular amine and water as the reaction medium. In some cases, it is also advantageous to carry out the reaction solely with water as the reaction medium.

The optimal water content of the reaction medium depends to a large extent upon the primary or secondary amine used (for example upon its basicity, reactivity, miscibility with water or its steric properties) and upon the sulphenamide formed (for example upon its stability under the reaction conditions, solubility) and may readily be determined by one skilled in the art in a few preliminary tests.

For example, cyclohexylamine preferably having a water content of from 20 to 100%, more preferably from 90 to 99% (disregarding the stoichiometric quantity of amine required for the reaction), is preferred as the reaction medium in the production of cyclohexylbenzothiazolyl sulphenamide from cyclohexylamine and 2-mercaptobenzothiazole or dibenzothiazyl-2,2'-disulphide.

By contrast, morpholine preferably having a water content of from 0 to 75%, more preferably from 10 to 50%, is preferred as a reaction medium in the production of morpholinylbenzothiazolyl sulphenamide from 2-mercaptobenzothiazole or dibenzothiazyl-2,2'-disulphide and morpholine.

A reaction medium of t-butylamine and water having a water content of from 0 to 85% is preferably used for the production of t-butylbenzothiazole sulphenamide from t-butylamine and 2-mercaptobenzothiazole or dibenzothiazolyl-2,2'-disulphide. In this case, a water content of from 0 to 20% is particularly preferred.

The ratio of primary or secondary amine to the 2-mercaptothiazole or dithiazolyl-2,2'-disulphide may also vary within wide limits in dependence upon the reaction medium used, although the amine should be used in stoichiometric quantity or in a stoichiometric excess to obtain a pure product. In general, the quantity of amine used amounts to 1.1-15 moles per mole of mercaptothiazole or 0.5 mole of dithiazolyl-2,2'-disulphide. The use of larger quantities of amine is less preferred on economic grounds.

In individual cases, for example where the primary or secondary amine shows inadequate miscibility with water or to increase the solubility of the catalyst, it is advantageous to add to the reaction mixture an organic solvent (for example alcohols) in a quantity which may readily be determined by one skilled in the art in a few preliminary tests. However, it is generally preferred not to use an additional solvent.

Metallic copper or a copper derivative is used as a catalyst in the process according to the present invention. The metallic copper is preferably used in the form of copper powder. Suitable copper derivatives are any monovalent or divalent inorganic, organic, simple or complex copper salts, except for the phthalocyanine complexes. Examples of suitable monovalent copper salts are copper (I) chloride, bromide and iodide, addition compounds of these copper (I) halides with carbon monoxide, complex copper (I) salts, such as alkali metal chlorocuprates, complex ammoniates of copper (I) cyanide, for example cyanocuprates such as potassium tricyanocuprate (I), double salts with copper (I) thiocyanate, copper (I) acetate, copper (I) sulphide and complex double sulphides of copper (I) sulphide and alkali metal polysulphides. Examples of suitable copper (II) salts are copper (II) chloride, bromide, sulphide, sulphate, nitrate, nitrite, thiocyanate, cyanide, Cu(II) salts of carboxylic acids, such as copper (II) acetate and also the complex ammoniates of copper (II) salts. Copper (I) oxide is another particularly suitable catalyst. Mixtures of several of the above-mentioned catalysts may, of course, also be used.

The necessary quantity of copper catalyst is surprisingly small, preferably amounting to from 0.005 to 5 mMoles permole of mercaptothiazole or per 0.5 mole of thiazolyl disulphide. It is possible to use even smaller quantities of catalyst, although in that case the reaction times are necessarily longer. Although larger quantities of catalyst increase the reaction velocity, they are not advisable because in that case the catalyst is in danger of contaminating the reaction product.

The reaction temperature is also important to the process. It is from 0° to 100° C. Although selectivity is particularly high at lower temperatures, the reaction velocity decreases to such an extent that reaction times of up to several days are required to obtain quantitative yields. However, a low reaction temperature, for example from 0° to 20° C., may be advantageous when it is desired to obtain a highly pure end product, so that a longer residence time of the reaction mixture in the reactor is acceptable to that end. At higher temperatures, the reaction velocity increases considerably, although at the same time selectivity is reduced as a result of over-oxidation or decomposition of the sulphenamide. This applies above all to temperatures above 100° C. and, to a lesser extent, even to temperatures below 100° C., but above 80° C. Accordingly, a high reaction temperature of from 80° to 100° C. will be advantageous when less stringent demands are imposed upon product purity, enabling a very high product throughout to be obtained in the reactor instead.

A particularly suitable temperature range for the process is from 10° to 90° C., temperatures from 20° to 80° C. being particularly preferred. The reaction may also preferably be carried out in a temperature range of 0° to 80° C.

In general, the process according to the present invention is carried out under oxygen pressures or oxygen partial pressures of at least 0.1 bar. As expected, the reaction velocity increases with increasing pressure. For economic and safety reasons, the process according to the present invention is preferably carried out under a pressure of from 1 to 10 bars.

The reaction time depends upon the process conditions and also upon the primary or secondary amine used. Under favorable conditions and where mercaptothiazoles are used, it amounts to a few minutes to 3 hours. Where dithiazolyl disulphides are used, the reaction times are shorter because only half the quantity of oxygen is required for oxidation.

The process according to the present invention is readily carried out by placing the reaction mixture under the oxygen or oxygen-containing gas under the temperature and pressure conditions indicated above or by introducing the oxygen or oxygen-containing gas into or through the reaction mixture which consists of primary or secondary amine, mercaptothiazole or dithiazolyl-2,2'-disulphide, copper catalyst, ammonia and, optionally, water and/or water-miscible solvent.

The mercaptothiazole or dithiazolyl-2,2'-disulphide and/or the primary or secondary amine may also be introduced into the reaction mixture during the reaction.

In most cases, the desired end product precipitates from the reaction mixture in solid form during the reaction itself or on completion of the reaction and after cooling and may be filtered off. In other cases, the product is obtained by dilution with water or by concentrating the reaction mixture. Liquid products are obtained in pure form by distillation or extraction.

Where the process according to the present invention is carried out on an industrial scale, it is advantageous to recirculate the mother liquor.

After the sulphenamide has been filtered off, the mother liquor may be replenished with 2,2'-disulphide and directly re-used almost indefinitely without adverse effect upon selectivity or yield. Accordingly, the process according to the present invention is particularly suitable for continuous working.

By means of the present invention, improved product yields (in most cases more than 95% of the theoretical yield) and high selectivities (from 95 to 100%) may be obtained. The products accumulate in highly pure form and, accordingly, may generally be used for the intended purpose without further purification. By virtue of the simple procedure involved, the high reaction velocity, the re-useability of the mother liquor and the possibility of continuous working, the present invention provides a highly economic process.

The process according to the present invention is further illustrated by the following Examples.

EXAMPLE 1

25 g (0.15 mole) of 2-mercaptobenzothiazole, 6 mg (0.03 mMole) of $Cu(OAc)_2 \cdot H_2O$, 170 g of water and 10.25 g (0.6 mole) of ammonia were introduced into a glass autoclave equipped with a double jacket for the circulation of a heating liquid, a thermometer, a pressure gauge and a stirrer. The reaction mixture was heated to 50° C., intensively stirred and placed under an oxygen pressure of 4.1 bars. 18.1 g (0.183 mole) of cyclohexylamine was introduced into the reaction mixture over a period of 3 hours. Uptake of oxygen was immediately recorded and a white deposit was formed. After 5 hours, the uptake of oxygen was only minimal; the reaction was terminated. The white deposit was filtered off, washed with ammonia solution and water and dried, giving 38.1 g of a product identical in its analytical data (elemental analysis, IR, $^1H$-NMR, MS) with N-cyclohexylbenzothiazole sulphenamide and of which the purity was found by high-pressure liquid chromatography to amount to 98% (m.p. 102° C.). The mother liquor still contained 0.7 g of unreacted mercaptobenzothiazole. Accordingly, the conversion amounted to 97.2% and the yield of cyclohexylbenzothiazole sulphenamide to 96.2% of the theoretical yield (selectivity 99%).

EXAMPLE 2

(Comparative Example)

The procedure was as in Example 1, except that no ammonia was added. Under these conditions, there was hardly any uptake of oxygen. After 5 hours, the mercaptobenzothiazole used was recovered substantially intact or in the form of its cyclohexyl ammonium salt.

EXAMPLE 3

The procedure was as in Example 1, except that 25 g (0.075 mole) of 2,2'-dibenzothiazolyl disulphide was used instead of 2-mercaptobenzothiazole. In addition, the cyclohexylamine was added over a period of 1.5 hours. After 3.5 hours, the oxygen uptake was minimal; the reaction was terminated. The yield of N-cyclohexylbenzothiazole sulphenamide amounted to 38.6 g, corresponding to 97.4% of the theoretical yield (product purity 98%).

EXAMPLE 4

20 g (0.12 mole) of 2-mercaptobenzothiazole, 12 mg of $Cu(OAc)_2 \cdot H_2O$ (0.06 mMole), 170 g of water and 10.25 g (0.6 mole) of ammonia were reacted with oxygen in the same way as described in Example 1, 13.2 g (0.132 mole) of cyclohexylamine being added over a period of 3 hours. The reaction temperature was 60° C. and the oxygen pressure 4 bars. After a reaction time of 3.5 hours, the mercaptobenzothiazole conversion was determined at 98.1%. The yield of cyclohexylbenzothiazole sulphenamide amounted to 96.2% of the theoretical yield.

EXAMPLE 5

In the reactor described in Example 1, a reaction mixture consisting of 16.7 g of mercaptobenzothiazole (0.1 mole), 49.6 g of cyclohexylamine (0.5 mole), 51 g of water, 1.7 g of ammonia (0.1 mole) and 60 mg of $Cu(OAc)_2 \cdot H_2O$ (0.3 mMole) was reacted with oxygen. The oxygen pressure was 4 bars, the reaction temperature 40° C. and the reaction time 2 hours. N-cyclohexylbenzothiazole sulphenamide accumulated in the form of a white crystalline deposit in a yield of 24.3 g, corresponding to 92% of the theoretical yield. The mercaptobenzothiazole conversion was determined by high-pressure liquid chromatography and amounted to 95.9%.

EXAMPLE 6

33.4 g of mercaptobenzothiazole (0.2 mole), 111.3 g of t-butylamine (1.52 moles), 3 g of water, 3.25 g of ammonia (0.19 mole) and 200 mg of $Cu(OAc)_2 \cdot H_2O$ (1 mMole) were introduced into the reactor described in Example 1. The reaction mixture was heated to 60° C., intensively stirred and placed under an oxygen pressure of 3 bars. Oxygen uptake was immediately recorded, coming to a stop after 70 minutes; the reaction was then terminated. A white solid (32.6 g) crystallized out on cooling the mother liquor. It was filtered off, washed and dried and was identical in its analytical data (elemental analysis, MS, IR, $^1H$-NMR) with N-t-butylbenzothiazole sulphenamide. Its purity was determined by high-pressure liquid chromatography and amounted to 98.4% (m.p. 108°–110° C.). The mother liquor contained another 14.9 g of the product which may be precipitated, for example by dilution with water, and isolated. The total yield of t-butylbenzothiazole sulphenamide thus amounted to 47.5 g, corresponding to 99.8% of the theoretical yield.

EXAMPLE 7

33.2 g of dibenzothiazolyl-2,2'-disulphide (0.1 mole), 111.3 g of t-butylamine (1.52 moles), 5.7 g of water, 3.25 g of ammonia (0.19 mole) and 200 mg of $Cu(OAc)_2 \cdot H_2O$ (1 mMole) were reacted with oxygen in the same way as in Example 6. The reaction temperature was 40° C. and the oxygen pressure 3.5 bars. After 75 minutes, the reaction was terminated (no further uptake of oxygen). The yield of t-butylbenzothiazole sulphenamide amounted to 99.9% of the theoretical yield (t-butyl-benzothiazole sulphenamide content: 98.9%).

EXAMPLE 8

In this Example, no water was added. The procedure was as in Example 6. The reaction mixture consisted of 33.4 g of mercaptobenzothiazole (0.2 mole), 114.3 g of t-butylamine (1.56 moles), 3.25 g of ammonia (0.19 mole) and 200 mg of Cu(OAc)$_2$.H$_2$O, and was reacted with oxygen (oxygen pressure 3.5 bars) at 40° C. The reaction time was 150 minutes. According to analysis by high-pressure liquid chromatography, the reaction mixture contained 45.9 g of t-butylbenzothiazole sulphenamide (yield 96.4% of the theoretical yield) which may be precipitated, for example by cooling and dilution with water, and isolated. In addition, the reaction mixture contained 0.57 g of unreacted mercaptobenzothiazole. Mercaptobenzothiazole conversion was 98.3%, selectivity 98%.

EXAMPLE 9

33.4 g of mercaptobenzothiazole (0.2 mole), 45.7 g of t-butylamine (0.63 mole), 3.25 g of ammonia (0.19 mole), 200 mg of Cu(OAc)$_2$.H$_2$O (1 mMole) and 60 g of water were reacted with oxygen in the same way as in Example 6. The reaction temperature was 40° C., the oxygen pressure 4 bars and the reaction time 150 minutes. The yield of t-butylbenzothiazole sulphenamide amounted to 90.8% of the theoretical yield and the mercaptobenzothiazole conversion was 93.6% (selectivity: 97%).

EXAMPLE 10

In this Example, the reaction was carried out at room temperature. 33.4 g of mercaptobenzothiazole (0.2 mole), 111.3 g of t-butylamine (1.52 moles), 3.0 g of water, 3.25 g of ammonia (0.19 mole) and 200 mg of Cu(OAc)$_2$.H$_2$O (1 mMole) were reacted with oxygen in the same way as in Example 6. The reaction temperature was 25° C. and the oxygen pressure 4 bars. After 6 hours, the reaction was terminated (no further uptake of oxygen). The yield of t-butylbenzothiazole sulphenamide amounted to 97.2% of the theoretical yield.

EXAMPLE 11

In this Example, air was used as the oxygen-containing gas. 33.4 g of mercaptobenzothiazole (0.2 mole), 108.6 g of t-butylamine (1.49 moles) 3.25 g of ammonia (0.19 mole), 5.7 g of water and 200 mg of Cu(OAc)$_2$.H$_2$O (1 mMole) were placed under 5 bars of air at 40° C. and reacted in the same way as in Example 6. After a reaction time of 180 minutes, the yield of t-butylbenzothiazole sulphenamide amounted to 95.1% of the theoretical yield and the mercaptobenzothiazole conversion to 95.5% (selectivity: 99.6%).

EXAMPLES 12-15

In these Examples, different copper catalysts were used. The procedure was as in Example 6, using in each case 33.4 g of mercaptobenzothiazole (0.2 mole), 108.6 g of t-butylamine (1.49 moles) and 5.7 g of water. The oxygen pressure was 3.5 bars in each case. The other reaction conditions and also the mercaptobenzothiazole conversion and yield of t-butylbenzothiazole sulphenamide are shown in the following Table.

| Example | Catalyst | (mMoles) | NH$_3$ (moles) | R-Temp (°C.) | R-time (mins.) | Conversion (%) | Yield (% of theor.) |
| --- | --- | --- | --- | --- | --- | --- | --- |
| 12 | CuSO$_4$ | (0.25) | 0.19 | 50 | 240 | 97.8 | 93.9 |
| 13 | CuCl | (1.0) | 0.05 | 60 | 220 | 99.4 | 98.9 |
| 14 | CuO | (0.5) | 0.19 | 60 | 190 | 96.9 | 94.6 |
| 15 | Cu—powder | (1.0) | 0.19 | 40 | 150 | 98.5 | 97.0 |

EXAMPLE 16

To produce N-cyclopentamethylene benzothiazole sulphenamide, a reaction mixture of 24.6 g of mercaptobenzothiazole (0.147 mole), 15.6 g of piperidine (0.183 mole), 200 g of water, 20.5 g of ammonia (1.2 moles) and 36 mg of Cu(OAc)$_2$.H$_2$O (0.18 mMole) was reacted with oxygen in the same way as described in Example 1. The reaction temperature was 40° C. and the oxygen pressure 4 bars. After 5 hours, the uptake of oxygen was only minimal and the reaction was terminated. The product deposit formed was filtered off, washed with dilute aqueous ammonia solution and water and dried. According to high-pressure liquid chromatography, it contained 98% of N-cyclopentamethylene benzothiazole sulphenamide. The product yield amounted to 93.7% of the theoretical yield. The mother liquor additionally contained 1.03 g of unreacted mercaptobenzothiazole (selectivity: 98%).

EXAMPLE 17

To produce N-isopropyl benzothiazole sulphenamide, 31.9 g of mercaptobenzothiazole (0.191 mole), 108.6 g of isopropylamine (1.83 mole), 1.64 g of ammonia (0.09 mole), 5.7 g of water and 100 mg of Cu(OAc)$_2$.H$_2$O (0.5 mMole) were reacted with oxygen (oxygen pressure 3 bars) at 40° C. in the same way as described in Example 8. The product (m.p. 94° C.) was obtained in a yield of 90.4% of the theoretical yield.

EXAMPLE 18

To produce morpholino-thiobenzothiazole, a reaction mixture consisting of 25.1 g of mercaptobenzothiazole (0.15 mole), 52.3 g of morpholine (0.6 mole), 5.1 g of ammonia (0.3 mole), 100 mg of Cu(OAc)$_2$.H$_2$O (0.5 mMole) and 36 ml of water was reacted with oxygen in the reactor described in Example 1. The oxygen pressure was 3.8 bars and the reaction temperature 50° C. After 2 hours, the reaction was terminated (minimal oxygen uptake), the deposit formed was filtered off, washed and dried and corresponded in its analytical data (elemental analysis, MS, IR $^1$H-NMR) to morpholinothiobenzothiazole (purity 98.2%, m.p. 82°–84° C.). The product yield amounted to 35.6 g, corresponding to 94.2% of the theoretical yield. The mother liquor additionally contained 0.7 g of unreacted mercaptobenzothiazole (selectivity: 97%).

EXAMPLE 19

24.9 g of dibenzothiazolyl-2,2'-disulphide (0.075 mole), 52.3 g of morpholine (0.6 mole), 2.6 g of ammonia (0.15 mole), 100 mg of Cu(OAc)$_2$.H$_2$O (0.5 mMole) and 27 ml of water were reacted with oxygen in the same way as in Example 18. The oxygen pressure was 4.0 bars, the reaction temperature 50° C. and the reaction time 140 minutes. Morpholino-thiobenzothiazole was obtained in a yield of 36.1 g, corresponding to 95.5% of the theoretical yield.

EXAMPLES 20–22

These Examples relate to the production of cyclohexyl benzothiazole sulphenamide using alcohols as additional solvents in each case. The procedure corresponded to that of Example 1; the oxygen pressure was 4.1 bars. The other reaction conditions, the mercaptobenzothiazole conversion and the yield of cyclohexylbenzothiazole sulphenamide are shown in the following Table:

| Example | Mercapto-benzothiazole (moles) | Cyclohexyl-amine (moles) | Water (g) | Alcohol | (g) | NH$_3$ (moles) | Cu(OAc)$_2$ (mMole) | Reaction temp. (°C.) | Reaction time (mins.) | Conversion (%) | Yield (% of theor.) |
|---|---|---|---|---|---|---|---|---|---|---|---|
| 20 | 0.20 | 0.22 | 132 | methanol | 36 | 0.8 | 0.06 | 50 | 210 | 97.3 | 94.2 |
| 21 | 0.15 | 0.18 | 114 | methanol | 54 | 0.6 | 0.08 | 50 | 150 | 96.1 | 92.8 |
| 22 | 0.15 | 0.18 | 135 | ethanol | 15 | 0.5 | 0.04 | 60 | 190 | 97.0 | 93.5 |

EXAMPLE 23

In this Example, the reaction was carried out at 80° C. 50 g (0.30 mole) of 2-mercaptobenzothiazole, 12 mg of Cu(OAc)$_2$.H$_2$O (0.06 mMole), 340 g of water and 20.4 g (1.2 moles) of ammonia were reacted with oxygen in the same way as described in Example 1, 34.0 g (0.343 mole) of cyclohexylamine being added over a period of 3 hours. The reaction temperature was 80° C. and the oxygen pressure 4 bars. After 3 hours, the reaction was terminated (no further oxygen uptake). The yield of N-cyclohexyl benzothiazole sulphenamide amounted to 85.5% of the theoretical yield.

Examples 24 to 25 show that, in the absence of a primary or secondary amine, no benzothiazole sulphenamide, only dibenzothiazolyl disulphide, is formed with ammonia.

EXAMPLE 24

(Comparative Example)

50 g (0.3 mole) of 2-mercaptobenzothiazole, 12 mg (0.06 mMole) of Cu(OAc)$_2$.H$_2$O, 20.4 g (1.2 moles) of ammonia and 320 g of water were introduced into the reactor described in Example 1. The reaction mixture was heated to 50° C., resulting in the formation of a clear solution which was intensively stirred and placed under an oxygen pressure of 4 bars. Uptake of oxygen was immediately recorded and a deposit accumulated through the formation of dibenzothiazolyl disulphide. After 1 hour, the reaction was terminated, the deposit filtered off, washed with aqueous ammonia and with water and dried in vacuo at 70° C., giving 47.7 g of a product which was identical in its analytical data (elemental analysis, IR, $^1$H-NMR and MS) with dibenzothiazolyl disulphide and which was found by chromatographic analysis to be 100% pure (m.p. 178° C.). According to analysis by gas chromatography, the mother liquor contained 1.8 g of unreacted 2-mercaptobenzothiazole. Accordingly, the 2-mercaptobenzothiazole conversion amounted to 96.4% and the yield of dibenzothiazolyl disulphide to 96.0% of the theoretical yield (selectivity: 99.6%).

EXAMPLE 25

(Comparative Example)

Following the procedure of Example 24, 50 g (0.3 mole) of 2-mercaptobenzothiazole, 8 mg (0.04 mMole) of Cu(OAc)$_2$.H$_2$O, 40.8 g (2.4 moles) of ammonia and 300 g of water were heated to 50° C., intensively stirred and placed under an oxygen pressure of 4 bars. Uptake of oxygen was immediately recorded and a deposit of dibenzothiazolyl disulphide was formed. After a reaction time of 2.5 hours, the 2-mercaptobenzothiazole conversion amounted to 95.4% and the yield of dibenzothiazolyl disulphide to 94.1% of the theoretical yield (selectivity: 98.6%).

What is claimed is:

1. A process for the production of benzothiazolyl sulphenamides corresponding to the following formula:

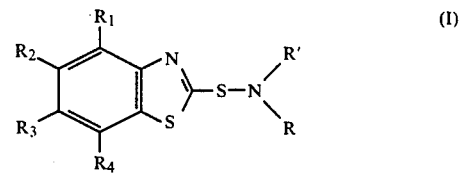
(I)

wherein:

R$_1$, R$_2$, R$_3$ and R$_4$, which may be the same or different, each represents hydrogen, chlorine, a nitro group, a hydroxyl group, a C$_1$–C$_6$ alkyl or alkoxy radical, a C$_6$–C$_{12}$ cycloalkyl or aryl radical; and R and R', which may be the same or different, each represents a C$_1$–C$_{18}$ straight, branched or cyclic alkyl group and may be attached to one another through a nitrogen atom, an oxygen atom or carbon atoms so that, with the amine nitrogen, they form a five-, six- or seven-membered heterocyclic group containing one or two nitrogen atoms or one nitrogen and one oxygen atom; or R represents a hydrogen atom and R' represents a straight, branched or cyclic C$_3$–C$_8$ alkyl group;

comprising reacting a 2-mercaptobenzothiazole or dibenzothiazolyl-2,2'-disulphide corresponding to the following formula:

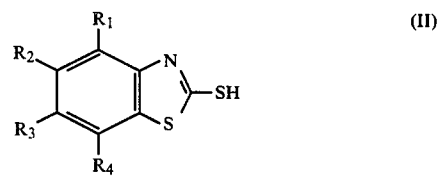
(II)

or

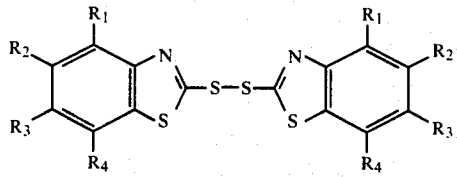

wherein $R_1$, $R_2$, $R_3$ and $R_4$ are as defined above; with a primary or secondary amine corresponding to the following general formula:

wherein R and R' are also as defined above; in the presence of (a) oxygen or an oxygen-containing gas and (b) copper or a copper derivative at temperatures from 0° to 100° C.; in the presence of ammonia and an excess of said primary or secondary amine or in the presence of ammonia and a mixture of said excess amine with at least one of water and a water-miscible organic solvent as the reaction medium.

2. A process as claimed in claim 1, wherein said ammonia is used in a quantity of from 0.2 to 25% by weight based on the weight of the reaction mixture.

3. A process as claimed in claim 2, wherein ammonia is used in a quantity of from 1 to 15% by weight based on the weight of the reaction mixture.

4. A process as claimed in claim 1, wherein $R_1$, $R_2$, $R_3$ and $R_4$ in formulae (II) and (III) each represent hydrogen.

5. A process as claimed in claim 1, wherein the reaction is carried out at a temperature of 0° to 80° C.

6. A process as claimed in claims 5, wherein the reaction is carried out at a temperature of 20° to 80° C.

7. A process as claimed in claim 1, wherein the reaction is carried out in the presence of 0.005 to 5 mMoles of copper catalyst, based on 1 mole of said 2-mercaptobenzothiazole or 0.5 mole of said dibenzothiazolyl-2,2'-disulphide.

8. A process as claimed in claim 1, wherein said 2-mercaptobenzothiazole or a dibenzothiazolyl-2,2'-disulphide is reacted with cyclohexylamine, t-butylamine or morpholine.

* * * * *

UNITED STATES PATENT AND TRADEMARK OFFICE
CERTIFICATE OF CORRECTION

PATENT NO. : 4,670,556

DATED : June 2, 1987

INVENTOR(S) : ZENGEL et al

It is certified that error appears in the above-identified patent and that said Letters Patent is hereby corrected as shown below:

Column 3, line 32, change "2-mercapto-6methylbenzothiazole," to --2-mercapto-6-methylbenzothiazole,--.

Column 14, in Claim 6, line 14, change "claims" to --claim--.

Signed and Sealed this

Sixth Day of October, 1987

Attest:

DONALD J. QUIGG

Attesting Officer

Commissioner of Patents and Trademarks